US010119926B2

(12) United States Patent
Aono

(10) Patent No.: US 10,119,926 B2
(45) Date of Patent: Nov. 6, 2018

(54) ANALYTICAL DEVICE AND AUTOSAMPLER USED IN THE SAME

(71) Applicant: SHIMADZU CORPORATION, Kyoto-shi, Kyoto (JP)

(72) Inventor: Akira Aono, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 241 days.

(21) Appl. No.: 15/032,348

(22) PCT Filed: Dec. 2, 2013

(86) PCT No.: PCT/JP2013/082368
§ 371 (c)(1),
(2) Date: Apr. 27, 2016

(87) PCT Pub. No.: WO2015/083218
PCT Pub. Date: Jun. 11, 2015

(65) Prior Publication Data
US 2016/0252472 A1 Sep. 1, 2016

(51) Int. Cl.
*G01N 25/20* (2006.01)
*G01N 1/44* (2006.01)
(Continued)

(52) U.S. Cl.
CPC .............. *G01N 25/20* (2013.01); *G01N 1/44* (2013.01); *G01N 30/24* (2013.01); *G01N 30/30* (2013.01); *G01N 2030/3076* (2013.01)

(58) Field of Classification Search
CPC .. G01N 25/20; G01N 25/4806; G01N 25/482; G01N 25/4826; G01N 25/4833;
(Continued)

(56) References Cited

U.S. PATENT DOCUMENTS 5,108,466 A * 4/1992 Klein .................... G01N 30/32
95/1
5,475,610 A * 12/1995 Atwood .............. B01L 3/50851
422/943
(Continued)

*Primary Examiner* — Lisa Caputo
*Assistant Examiner* — Philip Cotey
(74) *Attorney, Agent, or Firm* — Sughrue Mion, PLLC

(57) ABSTRACT

A heat retention start timing of each sample container is determined based on a room temperature detected by a room temperature sensor, and a starting temperature and an ending temperature of each sample at a time of programmed temperature analysis that are stored in an analysis condition storage section. Since cooling speed of each sample container varies depending on the room temperature, the cooling time (A12, B12, C12, . . . ) of each sample container may be predicted based on the ending temperature of each sample at the time of programmed temperature analysis, the starting temperature of a next sample at the time of the programmed temperature analysis, and the room temperature. By determining the heat retention start timing of each sample container according to the cooling time (A12, B12, C12, . . . ) of each sample container predicted in the above manner, a margin time (A13, B13, C13, . . . ) after the cooling time may be prevented from becoming unnecessarily long. Accordingly, the processing performance may be improved compared to a conventional configuration where the heat retention start timings of sample containers are shifted by fixed time intervals.

4 Claims, 5 Drawing Sheets

(51) Int. Cl.
*G01N 30/24* (2006.01)
*G01N 30/30* (2006.01)

(58) Field of Classification Search
CPC .......... G01N 1/44; G01N 30/24; G01N 30/30; G01N 2030/3076; B01L 3/00; G01K 13/12; G01K 1/20
See application file for complete search history.

(56) References Cited

U.S. PATENT DOCUMENTS

| | | | | |
|---|---|---|---|---|
| 5,508,204 A * | 4/1996 | Norman | ................ | G01N 30/30 210/198.2 |
| 5,558,790 A * | 9/1996 | Nazarian | ............ | G01N 25/4826 219/121.77 |
| 6,257,047 B1 * | 7/2001 | Grob | ...................... | G01N 30/16 422/89 |
| 7,803,635 B1 * | 9/2010 | Meece | ................ | G01N 1/4055 422/68.1 |
| 8,075,842 B1 * | 12/2011 | Meece | ................ | G01N 1/4055 422/67 |
| 2006/0108350 A1 * | 5/2006 | Yamauchi | .......... | G05D 23/1931 219/494 |
| 2007/0148780 A1 * | 6/2007 | Murata | .................... | B01L 7/00 436/147 |
| 2008/0038163 A1 * | 2/2008 | Boege | ...................... | B01L 7/52 422/600 |
| 2011/0290233 A1 * | 12/2011 | Iso | ........................ | G01N 30/30 126/273 R |
| 2012/0085148 A1 * | 4/2012 | Amirav | ................ | G01N 30/30 73/23.39 |
| 2013/0002250 A1 * | 1/2013 | Morgan | ................ | G01R 33/46 324/315 |
| 2013/0243652 A1 * | 9/2013 | Nishigaki | ........ | G01N 35/00584 422/68.1 |

* cited by examiner

ANALYTICAL DEVICE AND AUTOSAMPLER USED IN THE SAME

CROSS REFERENCE TO RELATED APPLICATIONS

This application is a National Stage of International Application No. PCT/JP2013/082368, filed on Dec. 2, 2013, the contents of all of which are incorporated herein by reference in their entirety.

TECHNICAL FIELD

The present invention relates to an analytical device for performing programmed temperature analysis by heating a sample, and an autosampler used in the same.

BACKGROUND ART

For example, with an analytical device that uses a sampling method such as a headspace method, a sample, which is an analysis target, is introduced into an analytical section by an autosampler from a sample container in which the sample is sealed. According to this type of analytical device, a liquid or solid sample in the sample container is vaporized due to heat of the sample container being retained, and an upper space (headspace) inside the sample container is filled with sample gas. By inserting a needle into the sample container in this state, the sample gas may be introduced into the analytical section via the needle.

In the case of continuously performing analysis of a plurality of samples, heat of each of a plurality of sample containers is retained, and sample gas is sequentially drawn out from each sample container (for example, see Patent Document 1). Samples may possibly contain a component which is decomposed when heat retention is continued, and thus the heat retention time is desirably fixed for each sample container. Normally, 30 minutes to several hours are required for heat retention, and the time may be longer than the analysis time of each sample. Accordingly, with the configuration described in Patent Document 1, heat retention is performed in an overlapped manner for a plurality of sample containers so as to improve the processing performance.

FIG. 5 is a diagram for describing a mode of autosampling by a conventional headspace method. In this example, a case is described in which a plurality of samples A, B, C, ... are sequentially introduced into a column of a gas chromatograph and programmed temperature analysis is continuously performed for the samples A, B, C, ....

The sample A is introduced into the column from a start timing $T111$ of the programmed temperature analysis, and analysis is performed until an end timing $T112$ of the programmed temperature analysis while increasing the temperature of the column. The programmed temperature analysis is thus performed only for a preset analysis time $A111$, and then the column is cooled. A cooling time $A112$ of the column changes depending on the room temperature, and the programmed temperature analysis of the next sample B is started after a margin time $A113$ has passed since a cooling end timing $T113$. From the start timing $T111$ of the programmed temperature analysis of the sample A to a start timing $T121$ of the programmed temperature analysis of the next sample B is a cycle time $A101$ of the sample A.

The sample B is introduced into the column from the start timing $T121$ of the programmed temperature analysis, and analysis is performed until an end timing $T122$ of the programmed temperature analysis while increasing the temperature of the column. The programmed temperature analysis is thus performed only for a preset analysis time $B111$, and then the column is cooled. In this example, due to a change in the room temperature, a cooling time $B112$ of the column after the programmed temperature analysis of the sample B is longer than the cooling time $A112$ of the column after the programmed temperature analysis of the sample A. A margin time $B113$ from a cooling end timing $T123$ until start of the programmed temperature analysis of the next sample C is reduced by the amount of increase in the cooling time $B112$, and a cycle time $B101$ of the sample B is thereby made the same as the cycle time $A101$ of the sample A.

The sample C is introduced into the column from the start timing $T131$ of the programmed temperature analysis, and analysis is performed until an end timing $T132$ of the programmed temperature analysis while increasing the temperature of the column. The programmed temperature analysis is thus performed only for a preset analysis time $C111$, and then the column is cooled. A cooling time $C112$ of the column after the programmed temperature analysis of the sample C is increased as in the case of the cooling time $B112$ of the column after the programmed temperature analysis of the sample B, and a margin time $C113$ is reduced to that extent. As a result, a cycle time $C101$ of the sample C is made the same as the cycle times $A101$, $B101$ of the samples A, B.

As described above, according to autosampling by a conventional headspace method, the cycle times $A101$, $B101$, $C101$, ... of the samples A, B, C, ... are the same. Specifically, the cycle times $A101$, $B101$, $C101$, ... of the samples A, B, C, ... are set to a relatively long time that allows a sufficient margin so that the cycle times $A101$, $B101$, $C101$, ... become the same even if the cooling times $A112$, $B112$, $C112$, ... are changed due to a change in the room temperature.

Heat retention times $A102$, $B102$, $C102$, ... of the samples A, B, C, ... are fixed. Since the cycle times $A101$, $B101$, $C101$, ... of the samples A, B, C, ... are the same, the start timings $T111$, $T121$, $T131$, ... of the programmed analysis of the samples A, B, C, ... are at a fixed cycle. Accordingly, heat retention start timings of the samples A, B, C, ... are also set while being shifted by fixed time intervals $D101$, $D102$, ....

PRIOR ART DOCUMENTS

Patent Documents

JP 2001-165920 A

SUMMARY OF THE INVENTION

Problems to be Solved by the Invention

However, according to the conventional configuration as described above, if the cooling time of a sample (for example, the cooling time $B112$, $C112$) is long, the cycle times $A101$, $B101$, $C101$, ... have to be set to a relatively long time. Accordingly, in the case where the cooling time of a sample is short (for example, the cooling time $A112$), the margin time $A113$ becomes unnecessarily long, and the processing performance is sometimes not sufficiently improved.

Furthermore, according to the conventional configuration as described above, the cycle times $A101$, $B101$, $C101$, ... have to be set by actually measuring the cooling times $A112$, B112, C112, . . . of the samples A, B, C, . . . in advance. Therefore, there is a problem that a burden is imposed on the operator.

The present invention has been made in view of the above circumstances, and has its object to provide an analytical device whose processing performance can be improved, and an autosampler used in the same. The present invention also has its object to provide an analytical device which is capable of reducing the burden on the operator, and an autosampler used in the same.

Means for Solving the Problems

An analytical device of the present invention includes an analytical section, an autosampler, an analysis condition storage section, a room temperature sensor and a heat retention start timing determination section. The analytical section is for performing programmed temperature analysis by heating a sample. The autosampler is for sequentially performing heat retention for a fixed period of time for a plurality of sample containers containing samples, and for sequentially introducing a sample into the analytical section starting from a sample container for which the fixed period of time has passed. The analysis condition storage section is for storing an analysis condition including a starting temperature and an ending temperature of each sample at a time of the programmed temperature analysis. The room temperature sensor is for detecting a room temperature. The heat retention start timing determination section is for determining a heat retention start timing of each sample container based on the room temperature detected by the room temperature sensor, and the starting temperature and the ending temperature of each sample at a time of the programmed temperature analysis that are stored in the analysis condition storage section.

According to such a configuration, the heat retention start timing of each sample container may be determined according to the room temperature detected by the room temperature sensor. Since cooling speed of each sample container varies depending on the room temperature, the cooling time of each sample container may be predicted based on the ending temperature of each sample at the time of programmed temperature analysis, the starting temperature of a next sample at the time of the programmed temperature analysis, and the room temperature.

By determining the heat retention start timing of each sample container according to the cooling time of each sample container predicted in the above manner, a margin time after the cooling time may be prevented from becoming unnecessarily long. Accordingly, the processing performance may be improved compared to a conventional configuration where the heat retention start timings of sample containers are shifted by fixed time intervals.

The analytical device may further include a cooling time calculation section. The cooling time calculation section is for calculating a cooling time after the programmed temperature analysis of each sample based on the room temperature detected by the room temperature sensor, and the starting temperature and the ending temperature of each sample at a time of the programmed temperature analysis that are stored in the analysis condition storage section. In this case, the heat retention start timing determination section may determine the heat retention start timing of each sample container based on the cooling time after the programmed temperature analysis of each sample calculated by the cooling time calculation section.

According to such a configuration, the cooling time of each sample container may be calculated by the cooling time calculation section based on the ending temperature of each sample at the time of the programmed temperature analysis, the starting temperature of a next sample at the time of the programmed temperature analysis, and the room temperature, and the heat retention start timing of each sample container may be determined based on the cooling time. Accordingly, since it is not necessary, as in the conventional case, to actually measure the cooling time of each sample container in advance, the burden on the operator may be reduced.

The analytical device may further include a cycle time calculation section. The cycle time calculation section is for calculating a cycle time from a start timing of the programmed temperature analysis of each sample to a start timing of the programmed temperature analysis of a next sample based on the cooling time after the programmed temperature analysis of each sample calculated by the cooling time calculation section. In this case, the heat retention start timing determination section may determine the heat retention start timing of each sample container based on the cycle time of each sample at a time of the programmed temperature analysis calculated by the cycle time calculation section.

According to such a configuration, the cycle time may be calculated from the calculated cooling time of each sample container, and the heat retention start timing of each sample container may be determined based on the cycle time. Accordingly, since it is not necessary, as in the conventional case, to set a fixed cycle time according to the cooling time of a sample, the burden on the operator may be effectively reduced.

An autosampler of the present invention is the autosampler for sequentially performing heat retention for a fixed period of time for a plurality of sample containers containing samples, and for sequentially introducing a sample into an analytical section starting from a sample container for which the fixed period of time has passed, the autosampler includes a heat retention start timing determination section. The heat retention start timing determination section is for determining a heat retention start timing of each sample container based on a room temperature detected by a room temperature sensor, and a starting temperature and an ending temperature of each sample at a time of programmed temperature analysis.

Effects of the Invention

According to the present invention, a margin time after a cooling time may be prevented from becoming unnecessarily long, and thus the processing performance can be improved compared to a conventional configuration where the heat retention start timings of sample containers are set to be shifted at fixed time intervals. Also, if the cooling time of each sample container is calculated, and the heat retention start timing of each sample container is determined based on the cooling time, since the cooling time of each sample container does not have to be actually measured in advance, as in the conventional case, the burden on the operator may be reduced.

MODE FOR CARRYING OUT THE INVENTION

Figure 1:
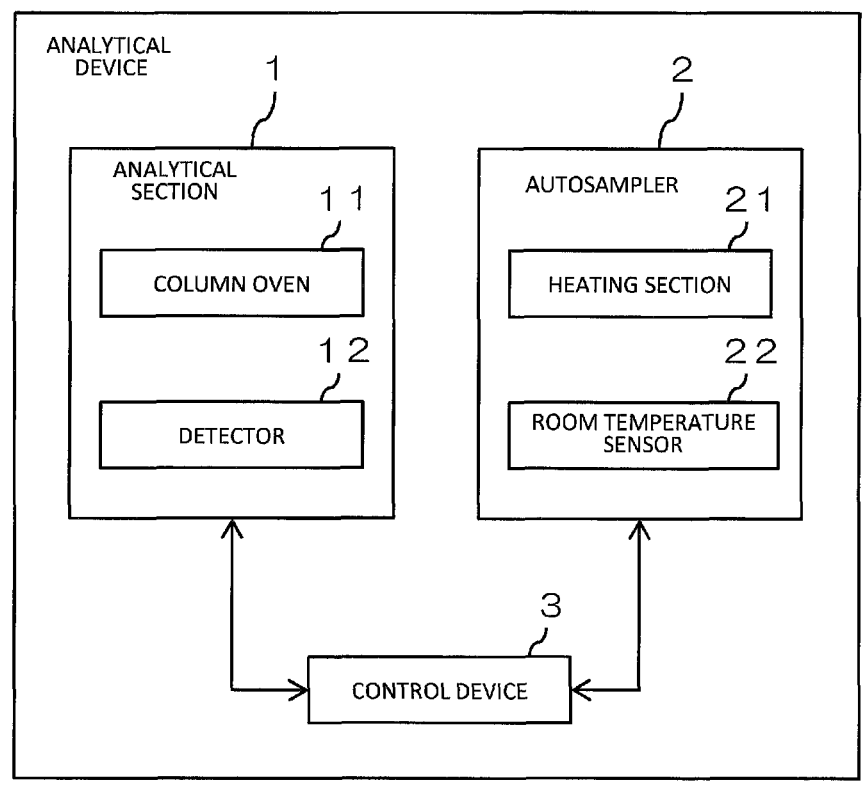
FIG. 1 is a block diagram showing an example configuration of an analytical device according to an embodiment of the present invention.

FIG. 1 is a block diagram showing an example configuration of an analytical device according to an embodiment of the present invention. This analytical device is a gas chromatograph for performing analysis by introducing sample gas into a column, and includes an analytical section 1, an autosampler 2, and a control device 3, for example.

The analytical section 1 includes a column oven 11 for accommodating a column, a detector 12 for detecting a sample component in sample gas, and the like. In the present embodiment, programmed temperature analysis may be performed by heating sample gas in the column by the column oven 11, and detecting, by the detector 12, a sample component separated in the course of passing through the column.

The autosampler 2 is for vaporizing a sample and for introducing the same into the analytical section 1, and a plurality of sample containers containing samples are set thereon. The autosampler 2 includes a heating section 21 for performing heat retention for the plurality of sample containers, a room temperature sensor 22 for detecting the room temperature, and the like. However, the room temperature sensor 22 may be installed at a position other than the autosampler 2 so long as it is capable of detecting the room temperature.

Each sample container is formed from a vial bottle and a cap, for example, and a liquid or solid sample is sealed inside the vial bottle by being placed inside the vial bottle and by attachment of the cap. When heat retention is performed for a sample container by the heating section 21 of the autosampler 2, the liquid or solid sample is vaporized inside the sample container, and an upper space (headspace) inside the sample container is filled with sample gas. By inserting a needle into the sample container in this state, the sample gas may be introduced into the analytical section 1 via the needle.

The control device 3 controls the operation of each section provided to the analytical device, such as the analytical section 1 and the autosampler 2. In the present embodiment, heat retention is sequentially performed for a plurality of sample containers set on the autosampler 2 for a fixed period of time under control of the control device 3, and sample gas is sequentially introduced into the analytical section 1 starting from the sample container for which the fixed period of time has passed.

Figure 2:
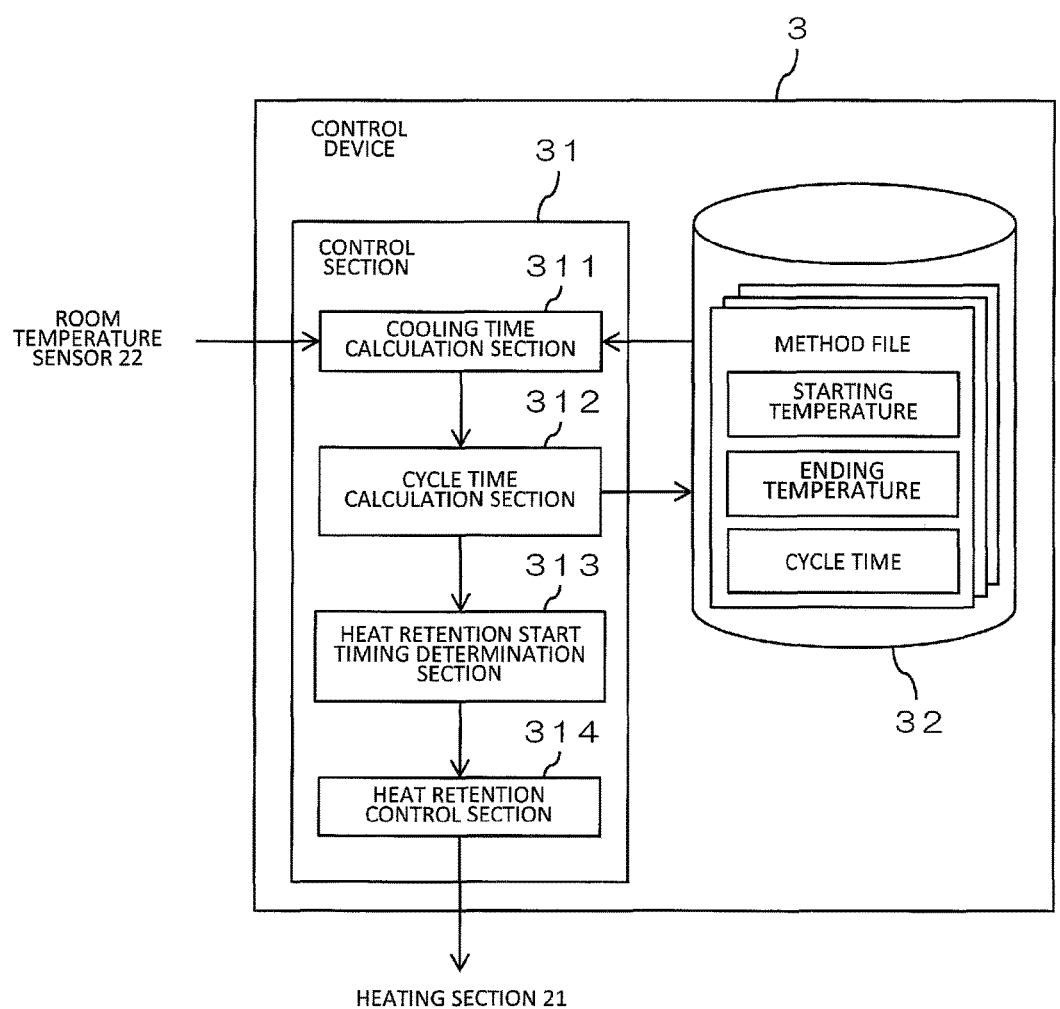
FIG. 2 is a block diagram showing an example configuration of a control device.

FIG. 2 is a block diagram showing an example configuration of the control device 3. The control device 3 is configured by a personal computer, for example, and includes a control section 31 and a storage section 32. The control section 31 includes a CPU (Central Processing Unit), for example, and functions as a cooling time calculation section 311, a cycle time calculation section 312, a heat retention start timing determination section 313, a heat retention control section 314, and so on by the CPU executing programs. The storage section 32 is configured by a hard disk or a RAM (Random Access Memory), for example.

According to the analytical device of the present embodiment, analysis is performed based on a method file including a plurality of types of analysis conditions, for example. The method file includes various analysis conditions that are necessary at the time of analysis of a sample, such as the starting temperature and the ending temperature of the sample at the time of programmed temperature analysis, a cycle time from a start timing of programmed temperature analysis of the sample to a start timing of programmed temperature analysis of the next sample, and so on. The storage section 32 functions as an analysis condition storage section for storing analysis conditions as mentioned above by storing a plurality of method files.

In the case of continuously performing programmed temperature analysis of samples, the column has to be cooled from the ending temperature of a sample at the end of the programmed temperature analysis to the starting temperature of the next sample at the time of the programmed temperature analysis. Cooling of the column is performed by air cooling or natural cooling, for example, and thus the cooling time of the column changes depending on the room temperature. The cooling time calculation section 311 calculates the cooling time after the programmed temperature analysis of each sample based on the room temperature detected by the room temperature sensor 22 and the starting temperature and the ending temperature, stored in the storage section 32, of each sample at the time of the programmed temperature analysis.

The cycle time calculation section 312 calculates the cycle time based on the cooling time, calculated by the cooling time calculation section 311, of each sample after the programmed temperature analysis. Specifically, the cycle time calculation section 312 calculates a cycle time including the analysis time, set in advance in the method file, of the programmed temperature analysis of each sample, the calculated cooling time after the programmed temperature analysis of each sample, and a predetermined margin time.

The cycle time in each method file stored in the storage section 32 is changed to the cycle time calculated by the cycle time calculation section 312. Accordingly, the cycle time is not always the same at the time of programmed temperature analysis of a sample, and is made different depending on the room temperature. Additionally, the margin time mentioned above is set to a relatively short fixed time which would prevent an error in the cooling time calculated by the cooling time calculation section 311 from affecting analysis of the next sample.

The heat retention start timing determination section 313 determines the heat retention start timing of each sample container based on the cycle time, calculated by the cycle time calculation section 312, of each sample at the time of the programmed temperature analysis. That is, if the cycle time of each sample at the time of the programmed temperature analysis is determined, the start timing of the programmed temperature analysis of each sample is determined, and heat retention for a sample container may be started a fixed heat retention time before the corresponding start timing.

The heat retention control section 314 controls heat retention for each sample container by the heating section 21 of the autosampler 2. The heat retention control section 314 causes heat retention for a sample container to be started at the heat retention start timing determined by the heat retention start timing determination section 313, and ends heat retention for the sample container after a sample is drawn out from the sample container at the start timing of the programmed temperature analysis of the sample.

Figure 3:
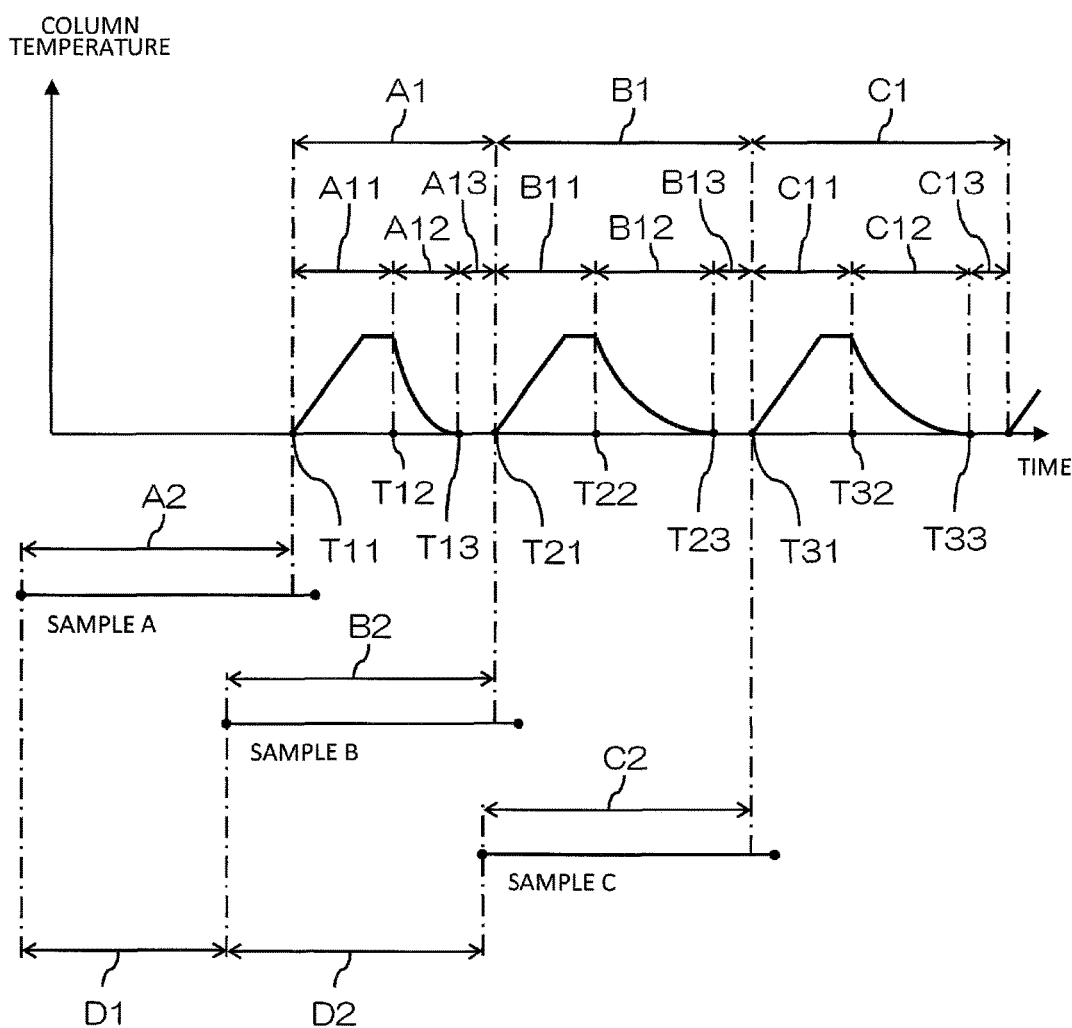
FIG. 3 is a diagram for describing a mode of autosampling by the analytical device in FIG. 1.

FIG. 3 is a diagram for describing a mode of autosampling by the analytical device in FIG. 1. In this example, a case is described in which a plurality of samples A, B, C, . . . are sequentially introduced into the column of the analytical section 1 and programmed temperature analysis is continuously performed for the samples A, B, C, . . . . Heat retention is performed for the samples A, B, C, . . . in an overlapped manner, and the processing performance may thereby be improved.

The sample A is introduced into the column from a start timing T11 of the programmed temperature analysis, and analysis is performed until an end timing T12 of the programmed temperature analysis while increasing the temperature of the column. The programmed temperature analysis is thus performed only for a preset analysis time A11, and then the column is cooled. A cooling time A12 of the column is a time that is determined in advance based on the room temperature, and the programmed temperature analysis of the next sample B is started after a fixed margin time A13 has passed since a cooling end timing T13. From the start timing T11 of the programmed temperature analysis of the sample A to a start timing T21 of the programmed temperature analysis of the next sample B is a cycle time A1 of the sample A.

The sample B is introduced into the column from the start timing T21 of the programmed temperature analysis, and analysis is performed until an end timing T22 of the programmed temperature analysis while increasing the temperature of the column. The programmed temperature analysis is thus performed only for a preset analysis time B11, and then the column is cooled. In this example, in view of a change in the room temperature, a cooling time B12 of the column after the programmed temperature analysis of the sample B is determined in advance to be longer than the cooling time A12 of the column after the programmed temperature analysis of the sample A. A margin time B13 is fixed regardless of the length of the cooling time B12, and thus a cycle time B1 of the sample B is longer than the cycle time A1 of the sample A.

The sample C is introduced into the column from a start timing T31 of the programmed temperature analysis, and analysis is performed until an end timing T32 of the programmed temperature analysis while increasing the temperature of the column. The programmed temperature analysis is thus performed only for a preset analysis time C11, and then the column is cooled. A cooling time C12 of the column after the programmed temperature analysis of the sample C is increased as in the case of the cooling time B12 of the column after the programmed temperature analysis of the sample B, but a margin time C13 is fixed. As a result, a cycle time C1 of the sample C is made longer than the cycle time A1 of the sample A.

As described above, in the present embodiment, the cycle times A1, B1, C1, . . . of the samples A, B, C, . . . are different according to the cooling times A12, B12, C12, . . . , On the other hand, heat retention times A2, B2, C2, . . . for the samples A, B, C, . . . are fixed. Since the cycle times A1, B1, C1, . . . of the samples A, B, C, . . . are different according to the cooling times A12, B12, C12, . . . , the start timings T11, T21, T31, . . . of the programmed temperature analysis of the samples A, B, C, . . . are not at a fixed cycle. Accordingly, the heat retention start timings of the samples A, B, C, . . . are also set while being shifted by different time intervals D1, D2, . . . .

Figure 4:
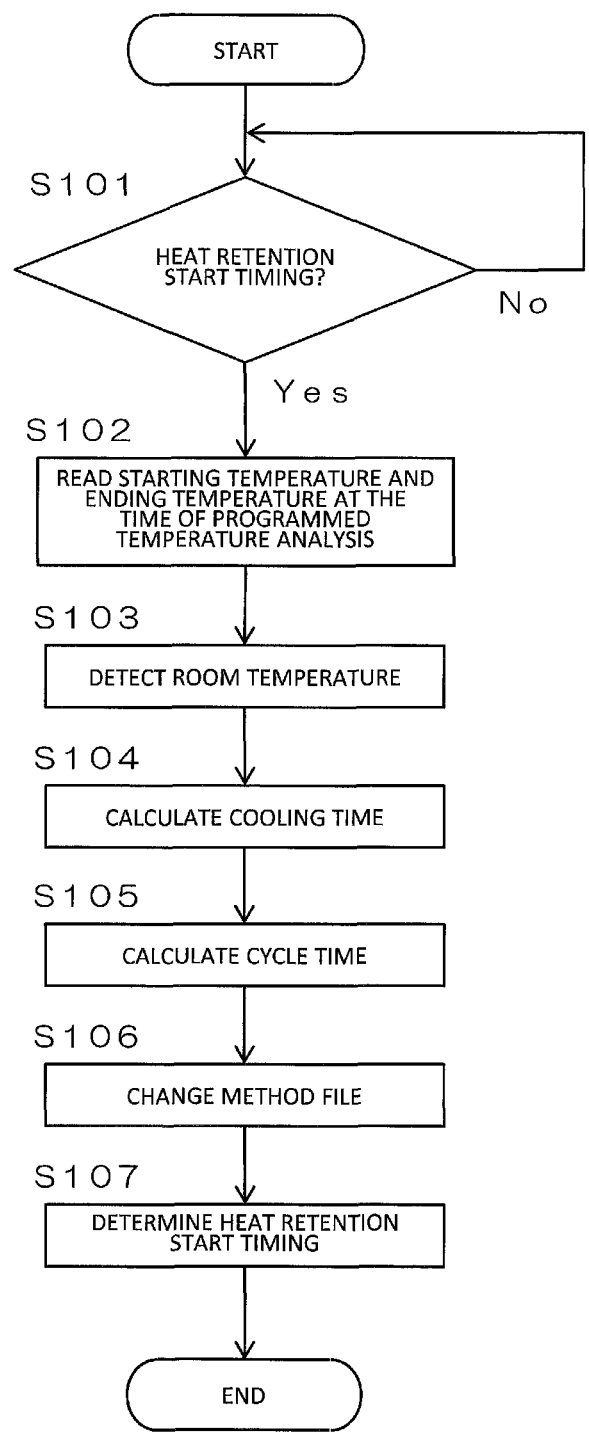
FIG. 4 is a flow chart showing an example of a process by a control section performed at the time of determining the heat retention start timing.

FIG. 4 is a flow chart showing an example of a process by the control section 31 performed at the time of determining the heat retention start timing. In the present embodiment, a case is described in which the heat retention start timing of a next sample is determined at the timing of start of heat retention for a sample. However, such a configuration is not restrictive, and the heat retention start timing may be determined at another timing so long as the heat retention start timing is determined after heat retention for a sample is started and before a timing when heat retention is to be started for the next sample.

In the following, a mode of determination of the heat retention start timing will be described with reference to FIGS. 3 and 4. First, when the heat retention start timing of the first sample A is reached (step S101: Yes), the ending temperature of the sample A at the time of the programmed temperature analysis and the starting temperature of the next sample B at the time of the programmed temperature analysis are read from the method file stored in the storage section 32 (step S102). Also, the room temperature at the time is detected by the room temperature sensor 22 (step S103).

Then, the cooling time A12 of the sample A is calculated based on the room temperature detected by the room temperature sensor 22 and the starting temperature and the ending temperature read from the storage section 32 (step S104). Moreover, the cycle time A1 is calculated by adding the analysis time A11 of the programmed temperature analysis of the sample A, the calculated cooling time A12 of the sample A, and the fixed margin time A13 (step S105).

The start timing T21 of the programmed temperature analysis of the next sample B is thereby determined, and a timing before the start timing T21 by the fixed heat retention time B2 is determined as the heat retention start timing of the sample B (step S107). Thereafter, the same process may be repeated at the heat retention start timings of the following samples B, C, . . . .

As described above, in the present embodiment, the heat retention start timing for each sample container may be determined according to the room temperature detected by the room temperature sensor 22. Since the cooling speed of each sample container varies depending on the room temperature, the cooling time A12, B12, C12, . . . of a sample container may be predicted based on the ending temperature of the sample A, B, C, . . . at the time of the programmed temperature analysis, the starting temperature of the next sample B, C, . . . at the time of the programmed temperature analysis, and the room temperature.

Figure 5:
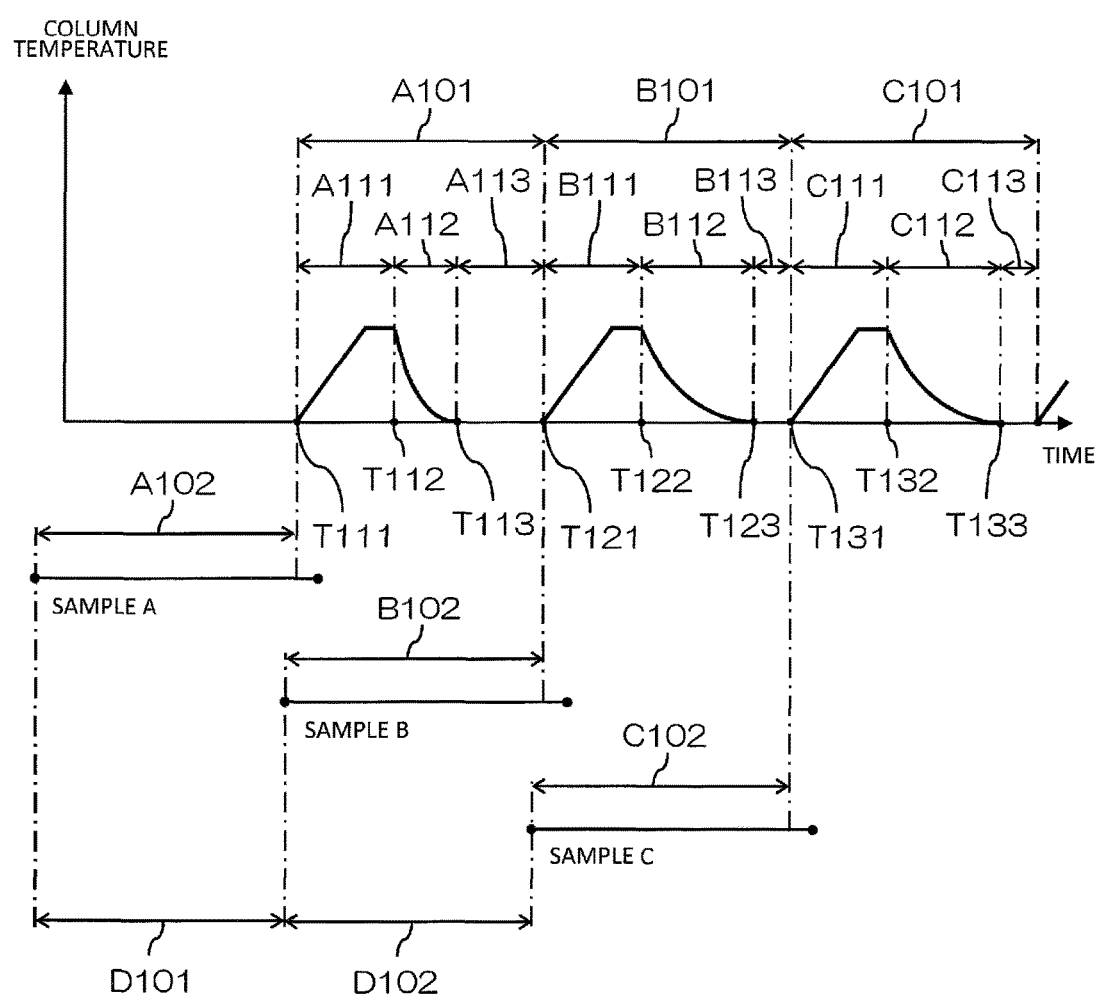
FIG. 5 is a diagram for describing a mode of autosampling by a conventional headspace method.

By determining the heat retention start timing of each sample container according to the cooling time A12, B12, C12, . . . of each sample container predicted in the above manner, the margin time A13, B13, C13, . . . after the cooling time may be prevented from becoming unnecessarily long. Accordingly, the processing performance may be improved compared to a conventional configuration where the heat retention start timings of the sample containers are shifted by fixed time intervals D101, D102, . . . (see FIG. 5).

Particularly, in the present embodiment, the cooling time A12, B12, C12, . . . of a sample container may be calculated by the cooling time calculation section 311 based on the ending temperature of the sample A, B, C, . . . at the time of the programmed temperature analysis, the starting temperature of the next sample B, C, . . . at the time of the programmed temperature analysis, and the room temperature, and the heat retention start timing of the sample container may be determined based on the cooling time A12, B12, C12, . . . . Accordingly, since it is not necessary, as in the conventional case, to actually measure the cooling times A112, B112, C112, . . . of the sample containers in advance (see FIG. 5), the burden on the operator may be reduced.

Furthermore, in the present embodiment, the cycle times A1, B1, C1, . . . may be calculated from the calculated cooling times A12, B12, C12, . . . of the sample containers, and the heat retention start timings of the sample containers may be determined based on the cycle times A1, B1, C1, . . . . Accordingly, since it is not necessary, as in the conventional case, to set fixed cycle times A101, B101, C101, . . . according to the cooling times A112, B112, C112, . . . of the samples (see FIG. 5), the burden on the operator may be effectively reduced.

In the embodiment described above, an analytical device in which the analytical section 1, the autosampler 2, and the control device 3 are integrally formed is described. However, such a configuration is not restrictive, and the functions of the control section 31 and the storage section 32 as shown in FIG. 2 may be provided to the autosampler 2 so as to separately configure an autosampler 2 to which the present invention is applied, for example.

Also, heat retention does not have to be performed for the samples A, B, C, . . . in an overlapped manner. That is, the present invention may be applied also to a configuration where heat retention for a next sample is started after heat retention for a sample is ended.

Furthermore, the present invention may be applied not only to a configuration where a sample is introduced into the analytical section 1 by the headspace method, but also to a configuration where a sample is introduced into the analytical section 1 by another mode. In this case, for example, an analytical device which introduces a sample into an analytical section by a thermal desorption method may determine a timing of starting heat retention for a sample tube filled with a sample by using the present invention.

DESCRIPTION OF REFERENCE SIGNS 1 analytical section
2 autosampler
3 control device
11 column oven
12 detector
21 heating section
22 room temperature sensor
31 control section
32 storage section
311 cooling time calculation section
312 cycle time calculation section
313 heat retention start timing determination section
314 heat retention control section
A1, B1, C1 cycle time
A2, B2, C2 heat retention time
A11, B11, C11 analysis time
   A12, B12, C12 cooling time
A13, B13, C13 margin time
D1, D2 time interval
T11, T21, T31 start timing of the programmed temperature analysis
T12, T22, T32 end timing of the programmed temperature analysis
T13, T23, T33 cooling end timing

The invention claimed is:

1. An analytical device comprising:
an analytical section for performing programmed temperature analysis by heating a sample;
an autosampler for sequentially heating a plurality of sample containers containing samples each for a fixed period of heating time, and for sequentially introducing a sample into the analytical section starting from a sample container for which the fixed period of heating time has passed;
an analysis condition storage section for storing an analysis condition including a starting temperature and an ending temperature of each sample at a time of the programmed temperature analysis;
a room temperature sensor for detecting a room temperature of a room surrounding the analytical device; and
a heat retention start timing determination section for determining a heating start timing of each sample container based on the room temperature detected by the room temperature sensor, and the starting temperature and the ending temperature of each sample at a time of the programmed temperature analysis that are stored in the analysis condition storage section.

2. The analytical device according to claim 1, further comprising a cooling time calculation section for calculating a cooling time after the programmed temperature analysis of each sample based on the room temperature detected by the room temperature sensor, and the starting temperature and the ending temperature of each sample at a time of the programmed temperature analysis that are stored in the analysis condition storage section,
wherein the heat retention start timing determination section determines the heating start timing of each sample container based on the cooling time after the programmed temperature analysis of each sample calculated by the cooling time calculation section.

3. The analytical device according to claim 2, further comprising a cycle time calculation section for calculating a cycle time from a start timing of the programmed temperature analysis of each sample to a start timing of the programmed temperature analysis of a next sample based on the cooling time after the programmed temperature analysis of each sample calculated by the cooling time calculation section,
wherein the heat retention start timing determination section determines the heating start timing of each sample container based on the cycle time of each sample at a time of the programmed temperature analysis calculated by the cycle time calculation section.

4. An autosampler for sequentially heating a plurality of sample containers containing samples for a fixed period of heating time, and for sequentially introducing a sample into an analytical section starting from a sample container for which the fixed period of heating time has passed, the autosampler comprising:
a heat retention start timing determination section for determining a heating start timing of each sample container based on a room temperature of a room surrounding the analytical device detected by a room temperature sensor, and a starting temperature and an ending temperature of each sample at a time of programmed temperature analysis.

* * * * *